(12) United States Patent
Polak et al.

(10) Patent No.: US 8,742,939 B2
(45) Date of Patent: Jun. 3, 2014

(54) ASPIRATING PARTICLE SENSOR FOR SMOKE DETECTION WITHIN AN ELECTRONICS ENCLOSURE

(71) Applicants: Scott Polak, Fort Collins, CO (US); Jeffrey Roberg, Longmont, CO (US); Michael Mueller, Loveland, CO (US)

(72) Inventors: Scott Polak, Fort Collins, CO (US); Jeffrey Roberg, Longmont, CO (US); Michael Mueller, Loveland, CO (US)

(73) Assignee: Advanced Energy Industries, Inc., Fort Collins, CO (US)

( * ) Notice: Subject to any disclaimer, the term of this patent is extended or adjusted under 35 U.S.C. 154(b) by 51 days.

(21) Appl. No.: 13/672,543

(22) Filed: Nov. 8, 2012

(65) Prior Publication Data

US 2014/0125487 A1    May 8, 2014

(51) Int. Cl.
*G08B 17/10*    (2006.01)

(52) U.S. Cl.
USPC ......... 340/628; 340/629; 340/630; 340/693.6

(58) Field of Classification Search
USPC .............. 340/628, 626, 627, 629, 630, 693.6
See application file for complete search history.

(56) References Cited

U.S. PATENT DOCUMENTS 6,107,925 A * 8/2000 Wong ............................ 340/628
6,166,647 A * 12/2000 Wong ............................ 340/628

* cited by examiner

*Primary Examiner* — Toan N Pham
(74) *Attorney, Agent, or Firm* — Neugeboren O'Dowd PC

(57) ABSTRACT

This disclosure describes systems, methods, and apparatus for rapidly detecting smoke or other particles or aerosols generated in any one or more compartments of a multi-compartment electronics enclosure. The herein disclosed system includes a particle sensor and an airflow controller that pulls air and particles from the one or more compartments through fluid pathways and into the particle sensor.

17 Claims, 7 Drawing Sheets

ASPIRATING PARTICLE SENSOR FOR SMOKE DETECTION WITHIN AN ELECTRONICS ENCLOSURE

FIELD OF THE DISCLOSURE

The present disclosure relates generally to particle detection. In particular, but not by way of limitation, the present disclosure relates to systems, methods and apparatuses for detecting smoke within an electronics enclosure.

BACKGROUND

Electronic systems inside of cleanrooms, especially power electronics systems, pose a contamination problem if any electronic components malfunction and begin to generate smoke or other undesirable aerosols or particles. If this smoke is able to leave the enclosure and contaminate the cleanroom (or other environment where low aerosol and/or particle count is preferred), the cleanroom may have to be shut down and cleaned—a process that can cost tens or hundreds of thousands of dollars in lost output.

It is possible to make completely enclosed electrical enclosures that could prevent smoke, if generated, from escaping into the cleanroom or other environment. However, such enclosures are difficult and expensive to make, and would require more complicated and expensive cooling systems. The simplicity and lack of expense for systems that cool electronics within an enclosure via exhausting warm/hot air into the cleanroom are preferred, and therefore there is a need to detect smoke generated from an electronics enclosure that vents.

Although smoke and other aerosol/particle detectors exist, a further challenge is that electronics within an electronics enclosure are sometimes isolated or partitioned such that zero or near-zero airflow between compartments exists. For instance, components such as an RF power amplifier and a control-board or motherboard are often isolated in separate compartments of an electronics enclosure used to power plasma processing tools. Use of a single smoke or aerosol/particle detector is hampered by this lack of airflow between compartments, and therefore unable to quickly detect smoke in other compartments.

This challenge is further complicated by the fact that system fans, and other cooling means, are often used to rapidly remove warm/hot air from the compartments into the external atmosphere. Thus, smoke escapes the enclosure faster than it moves between compartments, if at all. There is therefore a need for rapid smoke detection in any of the one or more compartments.

A possible solution is to locate a sensor in each of the compartments. However, due to limited space within such enclosures, as well as cost and complexity concerns, use of multiple sensors is not desirable. There is therefore a need for a smoke detection means that rapidly detects smoke generated in any one or more compartments of a multi-compartment electronics enclosure and does not take up excessive space.

SUMMARY OF THE DISCLOSURE

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

Some embodiments of the disclosure may be characterized as an electronics enclosure having multiple compartments, a particle sensor, and fluid pathways between each compartment and the particle sensor. Venting of the compartments in line with traditional methods for such an enclosure can be used to draw air from each compartment to the sensor where smoke particles, or other target particles or aerosols, can be detected. A warning indication or triggering of a safety mechanism can take place if a certain level of smoke particles or other target particles or aerosols are detected. In some embodiments, an air controller can be used to draw air and particles from the various compartments through the fluid pathways to the particle sensor.

Other embodiments of the disclosure may also be characterized as an electronic system comprising a multi-compartment electronics enclosure, a particle sensor, fluid pathways, and a detection and warning module. The multi-compartment electronics enclosure can have compartments, each having electronic components. The particle sensor can monitor particles that pass through or into contact with the particle sensor. The particle sensor can generate a signal describing the monitored particles and the particle sensor can experience a pressure differential between a first and a second side of the particle sensor. The fluid pathways can each connect one of the compartments to the particle sensor. The pressure differential can cause air and particles to be drawn out of each of the compartments through the fluid pathways and through or into contact with the particle sensor. The detection and warning module can receive the signal from the particle sensor and determine if a level of smoke in any of the compartment exceeds a threshold. If it does, then the detection and warning module can generate a warning indicator.

Other embodiments of the disclosure can be characterized as a method of detecting an undesired level of a target particle within a multi-compartment electronics enclosure. The method can include providing a particle sensor and generating a pressure differential between a first side and a second side of the particle sensor. The method can further include pulling air and particles from compartments of the multi-compartment electronics enclosure to the first side of the particle sensor and moving the air and particles from there to the second side. The method can also include monitoring the particles in the air as they move from the first to the second side of the particle sensor. The method can further include determining that a level of the target particle in any of the compartments exceeds a threshold. The method can yet further include triggering a safety mechanism of the multi-compartment electronics enclosure in response to the determining.

Yet other embodiments of the disclosure can be characterized as a non-transitory, tangible computer readable storage medium, encoded with processor readable instructions to perform a method for monitoring target particles within an electronics enclosure. The method can include generating a pressure differential between a first side and a second side of a particle sensor. The method can further include guiding particles from two or more compartments of the electronics enclosure from the first side to the second side of the particle sensor via the pressure differential. The method can additionally include monitoring the particles as they move from the first side to the second side of the particle sensor. The method can yet further include triggering a safety mechanism when the particles exceed a threshold.

BRIEF DESCRIPTION OF THE DRAWINGS

Various objects and advantages and a more complete understanding of the present invention are apparent and more readily appreciated by referring to the following detailed description and to the appended claims when taken in conjunction with the accompanying drawings:

DETAILED DESCRIPTION

The word "exemplary" is used herein to mean "serving as an example, instance, or illustration." Any embodiment described herein as "exemplary" is not necessarily to be construed as preferred or advantageous over other embodiments.

For the purposes of this disclosure an "airflow controller" includes any device that can manipulate a flow of air. Pumps and fans are two non-limiting examples of airflow controllers.

For the purposes of this disclosure a "particle sensor" is a device that monitors levels of a target particle or aerosol. Target particles can include smoke, for instance. Monitoring can be direct or indirect. For instance, the level of the target particle can be measured in terms of particle flux or particles per unit of air flux, to name two non-limiting examples. In a further example, light can be passed through a volume of air and a percent of light obscured or reflected can be used to determine these values.

This disclosure discusses an electronics enclosure having multiple compartments with zero or near-zero airflow between compartments, and modified to include a particle sensor configured to quickly detect an abnormal level of smoke particles, or other target particles/aerosols. The particle sensor quickly detects smoke or other particles/aerosols by monitoring airflows from a plurality of fluid pathways that bring air from the various compartments to the sensor. A warning indicator can be generated by auxiliary electronics in response to particle levels exceeding a threshold, and the warning indicator, in some cases, can trigger a safety mechanism, such as a shutdown of electronics in the enclosure so as to not disperse the particles throughout the facility.

Figure 1:
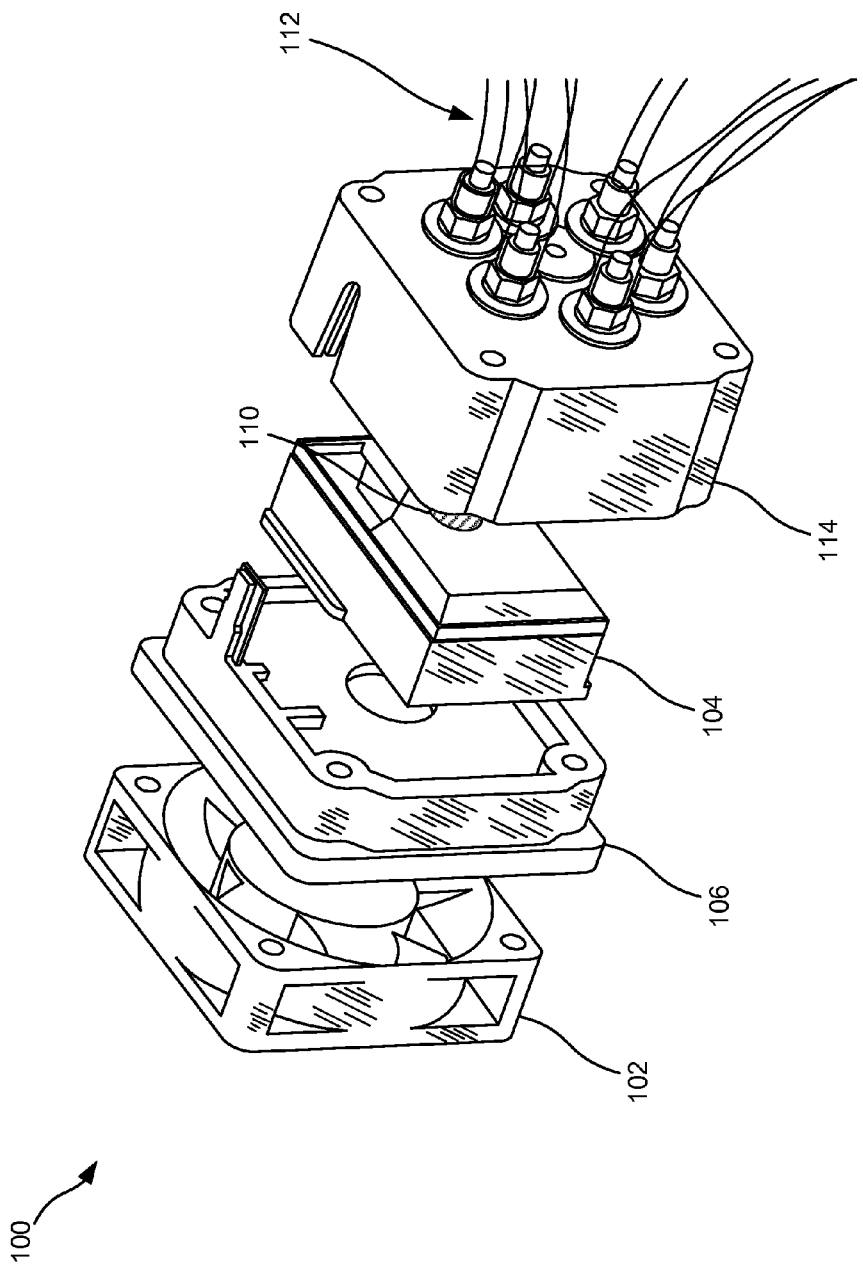
FIG. 1 illustrates a particle sensor system.

FIG. 1 illustrates a particle sensor system 100. The particular sensor system 100 can include a fan 102 or other air controller that creates a pressure differential between a first side and a second side of a particle sensor 104. The pressure differential can pull air from various compartments through a plurality of pathways 112 to the sensor 104. The particle sensor 104 can be arranged between a first manifold 106 and optionally a second manifold 114, both of which are configured to assist in directing airflow to and from the particle sensor 104.

An air controller 102 includes any device or means capable of providing a pressure differential that draws air through the system 100, and in particular draws air through, or into contact with, a particle sensor 104. The air controller 102 can expel air and particles that pass through, or come into contact with, the particle sensor 104 to an environment external to the electronics enclosure (not illustrated) as well as back into the enclosure.

The particle sensor 104 can take a variety of forms, such as optical or ionizing, to name two examples. In one embodiment, it is configured to detect a number of, rate of, or density of particles or aerosols in air that contact the particle sensor 104 or passes through the particle sensor 104. In a preferred embodiment, the particle sensor 104 can at least detect smoke particles, and distinguish these from dust and other particles and aerosols. The particle sensor 104 can be optical, photoelectric, ionizing, or aerosol-sensing, to name a few non-limiting examples. Off-the shelf as well as custom sensors can be implemented.

The particle sensor 104 can include a sensing pathway 110 through which air from the fluid pathways 112 passes, and in which the particle sensor 104 monitors particles and/or aerosols that pass through the sensing pathway 110. The location and shape of the sensing pathway 110 in FIG. 1 is illustrative only, and various other sensing pathways 110 and configurations of the sensing pathway 110 can be implemented without departing from the scope of this disclosure.

The particle sensor 104 output can represent particle count and/or aerosol density. In one embodiment, this output signal can be time averaged or integrated to differentiate between different types of particles and aerosols. In one embodiment, this integration or averaging is performed in order to differentiate between dust and smoke particles as well as to quantify a severity of the smoke. For instance, where an integrated voltage output from the particle sensor 104 exceeds a threshold, the system 100 has detected a level of smoke that indicates that a warning or system shutdown is in order. As a further example, dust particles tend to cause discrete signal pulses from the particle sensor 104, while smoke tends to cause substantially continuous high voltage signals to be produced. As such, when time-integrating signals from the particle sensor 104, smoke particles will cause the integration value to rise very quickly as compared to the integration value associated with dust particles. This is just one of many algorithms that can be used to distinguish smoke particles from other types of particles.

The fluid pathways 112 can be configured to carry a gas from a first location to a second location without any loss of the gas or particles in the gas between the first and second location. The fluid pathways 112 can be axially arranged relative to the sensing pathway 110 to encourage a linear flow of air into the sensing pathway 110. In some embodiments, the arrangement of the fluid pathways 112 relative to each other and the sensing pathway 110 is such that a minimum amount of air flow mixing occurs.

The second manifold can couple to the fluid pathways 112 and direct air exiting the fluid pathways 112 to the particle sensor 104, and in particular, through the sensing pathway 110.

Figure 2:
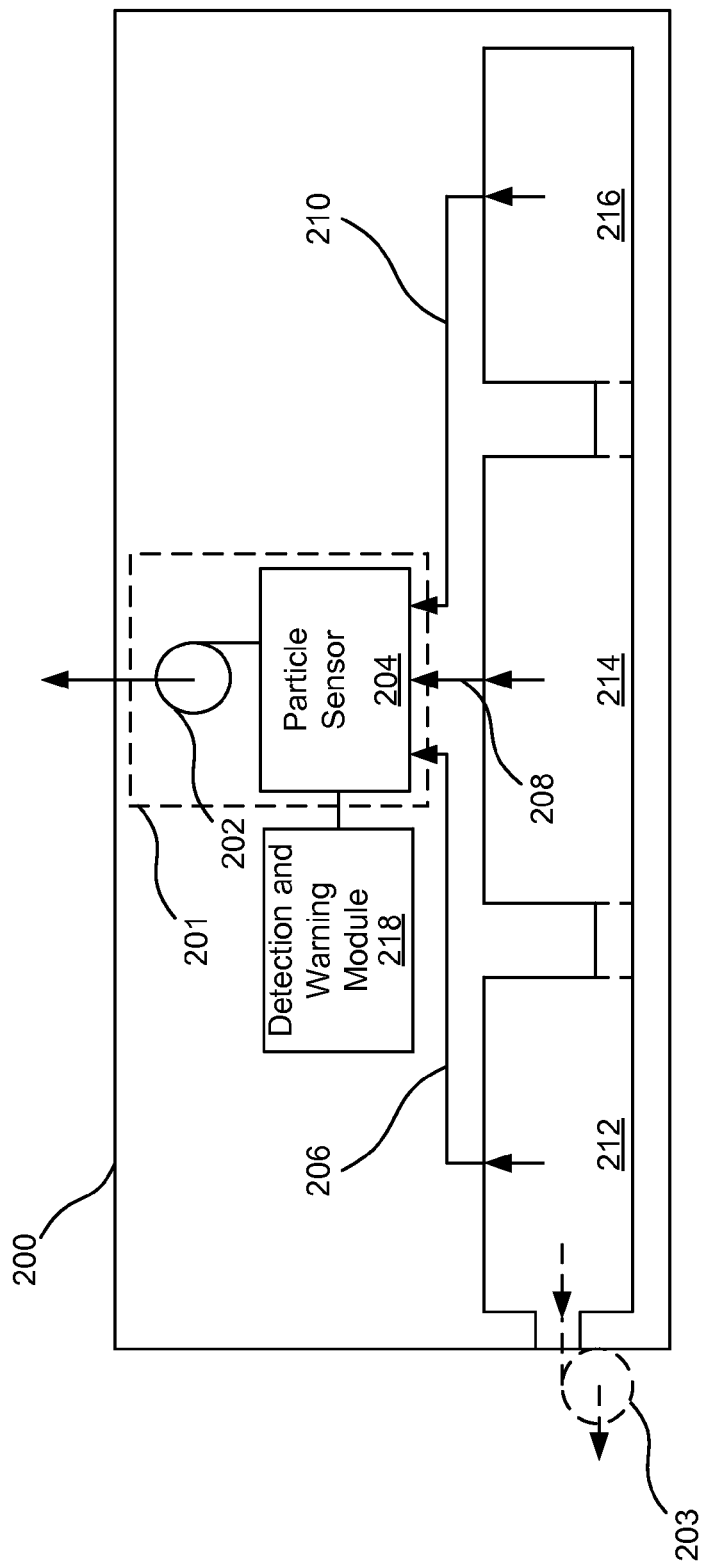
FIG. 2 illustrates an electronics enclosure having a plurality of compartments, a particle sensor, an airflow controller, and a plurality of fluid pathways from the compartments to the particle sensor.

FIG. 2 illustrates an electronics enclosure 200 having a plurality of compartments 212, 214, 216, a particle sensor system 201, and a plurality of fluid pathways 206, 208, 210 from the compartments 212, 214, 216 to a particle sensor 204 of the particle sensor system 201. Each of the plurality of compartments 212, 214, 216 can be in fluid communication with adjacent compartments 212, 214, 216, however, and as the dotted vertical lines suggest, in some cases, the compartments 212, 214, 216 may be in complete fluid isolation from each other (e.g., air cannot move between compartments 212, 214, 216). A fluid pathway 206, 208, 210 is connected between each compartment 212, 214, 216 and the particle sensor 204, although in some embodiments (not illustrated), more than one fluid pathway 206, 208, 210 may connect each compartment 212, 214, 216 and the particle sensor 204. An airflow controller 202 of the particle sensor system 201 pulls air from the compartments 212, 214, 216 through the fluid pathways 206, 208, 210, through the particle sensor 204, or into contact with the particle sensor 204, and out of the electronics enclosure 200. In an embodiment, an optional system fan 203 may be included that removes warm/hot air from the electronics enclosure 200 in order to cool the electronics. The system fan 203 can also be implemented as any type of air controller.

The electronics enclosure 200 may further include a detection and warning module 218 that determines if there is smoke being generated in any of the compartments 212, 214, 216 and if so, generates a warning indication. The particle sensor 204 can generate a signal based on the number, rate, or density of particles or aerosols passing through it, or coming into contact with it, and passes this signal to the detection and warning module 218. In some embodiments, this signal is an analog voltage where each particle causes a voltage peak. The detection and warning module 218 carries out an algorithm that determines whether abnormal levels of smoke are being generated, for instance, via integration or averaging of the signal and comparison to a threshold.

If the detection and warning module 218 determines that an abnormal level of smoke, or other target particles or aerosols, is being generated, then it generates a warning indication. The warning indication can be in the form of an audible (e.g., audible alarm) or visible signal (e.g., blinking light or message on a display). The warning indication can also trigger a safety mechanism such as a partial or full shutdown of electronics of the electronics enclosure.

A level of smoke, or other target particles or aerosols, considered 'abnormal' is a level that can be set by a user, and may depend on the type of environment in which the electronics enclosure resides. For instance, abnormal levels of smoke in a class 1000 cleanroom are likely higher than in a class 1 cleanroom.

In some embodiments, two or more fluid pathways may connect a single compartment to the particle sensor 204. For instance, given two compartments of differing sizes, two fluid pathways may extract air and particles from the large compartment while only a single fluid pathway 212 extracts air and particles from the smaller compartment. The motivation of such an embodiment, and similar embodiments, is to enable air flow rates to the particle sensor 204 to be proportional to a volume of a compartment. If such was not carried out, then the particle counts in the particle sensor 204 may under or overestimate an actual particle count in a compartment. In another embodiment, two or more fluid pathways may be used to extract air and particles or other aerosols from a compartment where that compartment has poor air circulation due to impeding structures such as stacks of memory chips, large inductors, cooling fans, or other impediments to airflow.

The particle sensor system 201 can further include one or more manifolds (not illustrated), such as the manifolds 106 and 114 in FIG. 1 to help direct the flow of air and particles or other aerosols in the particle sensor system 201. In some embodiments, the particle sensor 204 and the airflow controller 202 need not be part of a particle sensor system 201, and instead can be discrete components. Examples of such arrangements will be illustrated in FIGS. 3 and 4. However, it should be understood that even in the embodiments illustrated in FIGS. 3 and 4, the particle sensors and the airflow controllers could be part of a particle sensor system 201.

The air controller 202 and the particle sensor 204 are illustrated as being within the electronics enclosure 200, but in other embodiments, one or both of these can be arranged outside of the electronics enclosure 200. For instance, in FIG. 3, both the particle sensor 304 and the air controller 302 are arranged outside the electronics enclosure 300. One or both of the particle sensor 304 and the air controller 302 can be coupled to the electronics enclosure 300 or coupled to each other. A detection and warning module 318 can also be arranged external to, and possibly coupled to, the electronics enclosure 300. In some embodiments, the detection and warning module 318 can be arranged within the electronics enclosure 300. The detection and warning module 318 can receive signals from the particle sensor 304 and determine if a level of smoke in any one or more of the compartments 312, 314, 316 has exceeded a threshold. If so, a warning indication can be generated or a safety mechanism (e.g., electronics shutdown or power cutoff) can be triggered.

Figure 4:
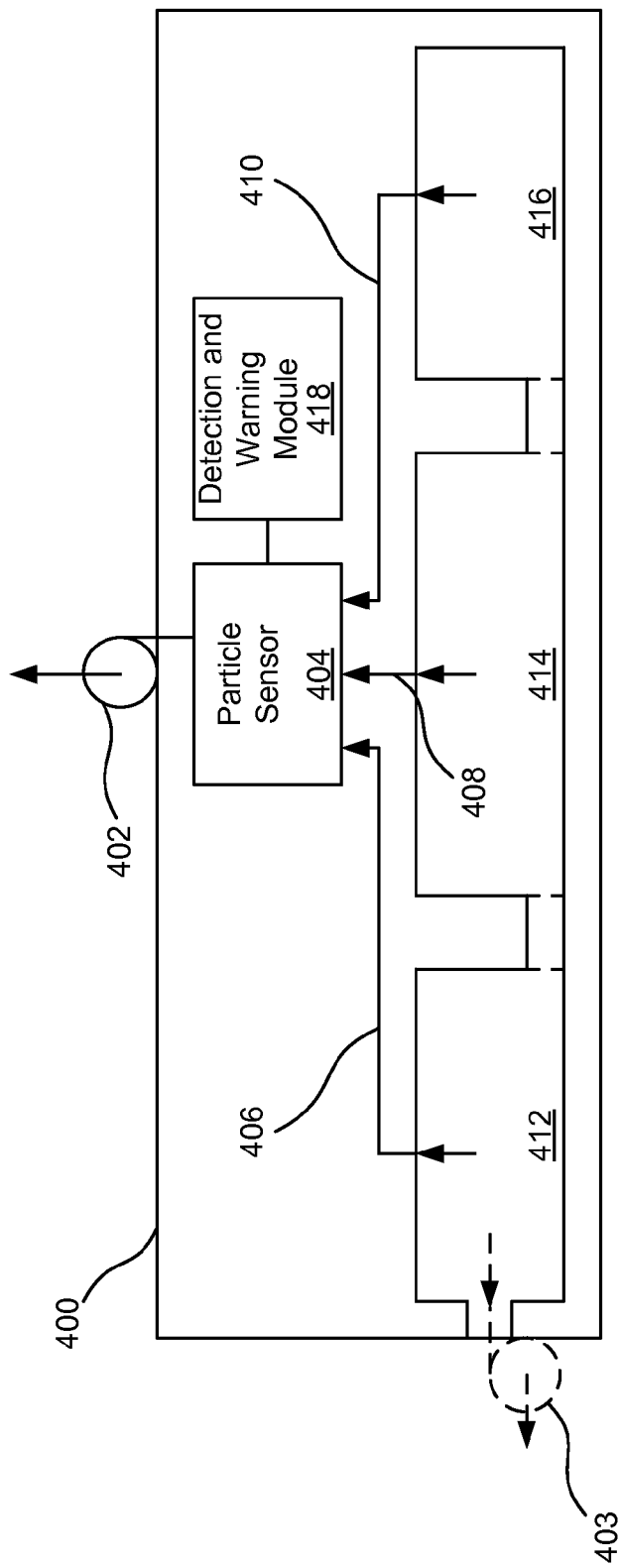
FIG. 4 illustrates yet another electronics enclosure having a plurality of compartments, a particle sensor, an airflow controller, and a plurality of fluid pathways from the compartments to the particle sensor.

As another example, in FIG. 4 the particle sensor 404 is arranged within the electronics enclosure 400 and the air controller 402 is arranged outside the electronics enclosure 400. In such, an embodiment, the air controller 402 can be coupled to the electronics enclosure 400. A detection and warning module 418 can also be arranged within the electronics enclosure 400. The detection and warning module 418 can receive signals from the particle sensor 404 and determine if a level of smoke in any one or more of the compartments 412, 414, 416 has exceeded a threshold. If so, a warning indication can be generated.

Returning to FIG. 2, in other embodiments, one or both of the particle sensor 204 and the air controller 202 can be arranged within one of the compartments 212, 214, 216. For instance, these embodiments may be used where the electronics enclosure 200 is configured such that the only room where the particle sensor 204 and air controller 202 can be located is within one of the compartments 212, 214, 216.

In some embodiments, the optional system fan 203 moves a larger or substantially larger volume of (or moves a greater rate of) air than the air controller 202. The optional system fan 203 is illustrated as being coupled to, but external to, the electronics enclosure 200. In other embodiments, the optional system fan 203 can be arranged within the electronics enclosure 200, for instance, within one of the compartments 212, 214, 216 (e.g., see FIG. 3). Furthermore, the optional system fan 203 is illustrated as removing air from the compartment 212, but not necessarily from the other two compartments 214, 216. In practice, the optional system fan 203 is configured to remove warm/hot air from any one or more of the compartments 212, 214, 216 and therefore should not be considered limited to removing air from just compartment 212.

Figure 3:
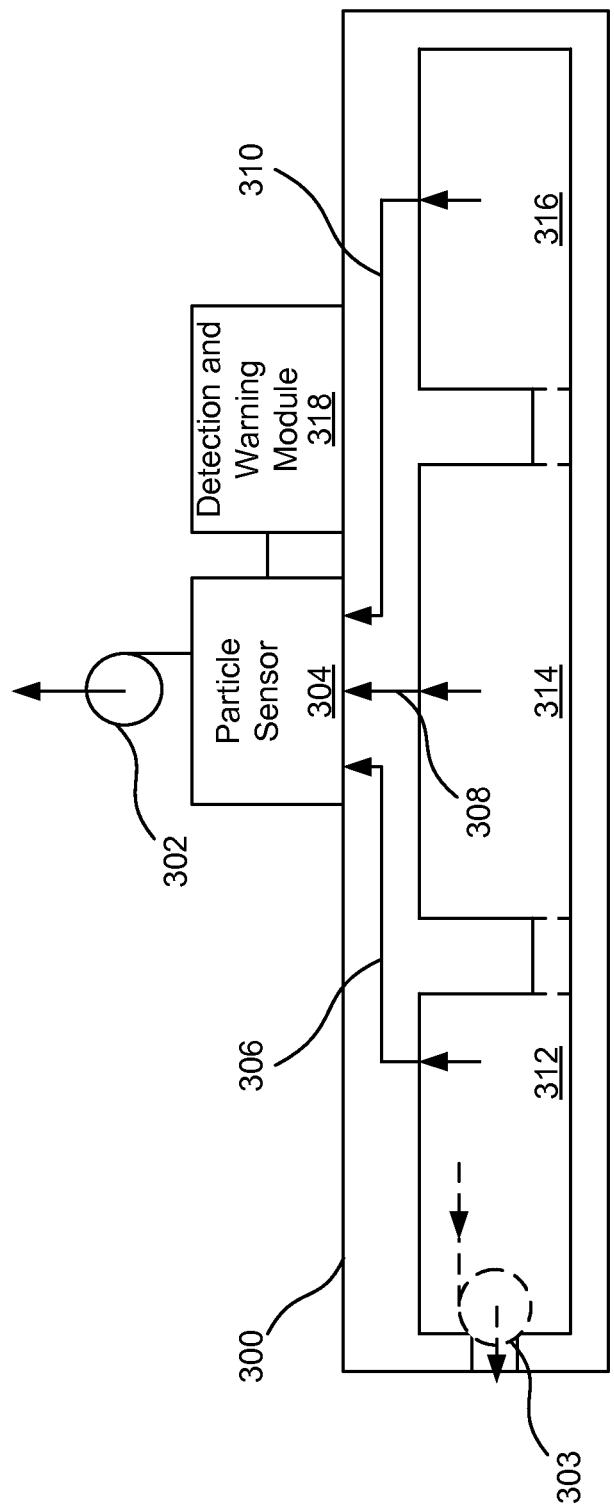
FIG. 3 illustrates an embodiment of an electronics enclosure where an optional system fan is arranged within one of the compartments.

FIG. 3 illustrates an embodiment where an optional system fan 303 is arranged within one of the compartments 312 while the particle sensor 304, the airflow controller 302, and the detection and warning module 318 are arranged external to the electronics enclosure 300. In this embodiment, any one or more of the particle sensor 304, the airflow controller 302, and the detection and warning module 318 can be separate from the electronics enclosure 300. The system fan 303 again draws warm/hot air from the compartments 312, 314, 316 and moves the warm/hot air outside the electronics enclosure 300.

Figure 5:
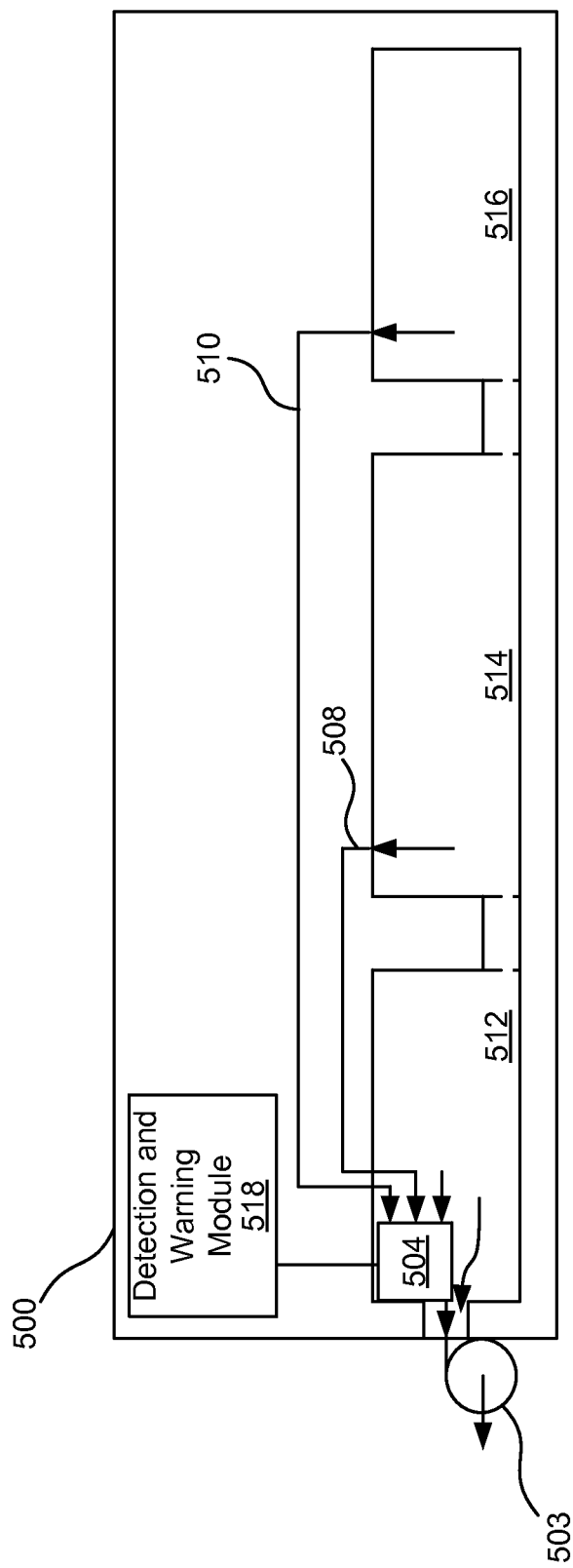
FIG. 5 illustrates yet another variation on the electronics enclosure of FIG. 2.

FIG. 5 illustrates yet another variation on the electronics enclosure of FIG. 2. Here, a system fan 503 is located external to the electronics enclosure 500, but could also be arranged within the electronics enclosure 500 as long as it pulls air from within the enclosure 500 to outside the enclosure 500 so as to cool electronics of the electronics enclosure 500. A particle sensor 504 can be arranged within one of the compartments 512 and receives air from other compartments 514, 516 via fluid pathways 508, 510. Air from the compartment 512 in which the particle sensor 504 is located is pulled into the particle sensor 504 with or without a fluid pathway. The air from the plurality of compartments 512, 514, 516 is pulled into and through, or at least into contact with, the particle sensor 504 and then pulled out of the electronics enclosure 500 via a pressure differential across the particle sensor 504 generated by the system fan 503. In other words, the particle sensor 504 passively relies on the natural pressure differences generated by the system fan 502 to move air through the particle sensor 504. This embodiment, removes the need for an air controller (e.g., 202) dedicated to moving air through the particle sensor 504.

In an embodiment, the electronics enclosure 500 can further include a detection and warning module 518, which receives signals from the particle sensor 504 and determines if a level of smoke or other target particles or aerosols in any one or more of the compartments 512, 514, 516 has exceeded a threshold. If so, a warning indication can be generated.

In some embodiments, there can be more than one system fan 503, and in other embodiments, one or more system fans 503 can push air through the particle sensor 504 rather than pull air through it.

Although FIG. 5 only illustrates a single system fan 503, more than one system fan 503 can be utilized and in such cases, the particle sensor 504 can be arranged anywhere in which air flow caused by the one or more system fans 503 draws air from the compartments 512, 514, 516 through, or into contact with, the particle sensor 504.

Although three compartments are illustrated in FIGS. 2-5, three fluid pathways are illustrated in FIGS. 2-4, and two fluid pathways are illustrated in FIG. 5, more or less than these numbers can be implemented in other embodiments. Furthermore, the shapes, sizes, and locations of the compartments and the fluid pathways are illustrative only, and in other embodiments these can all be changed to suit various needs.

Figure 6:
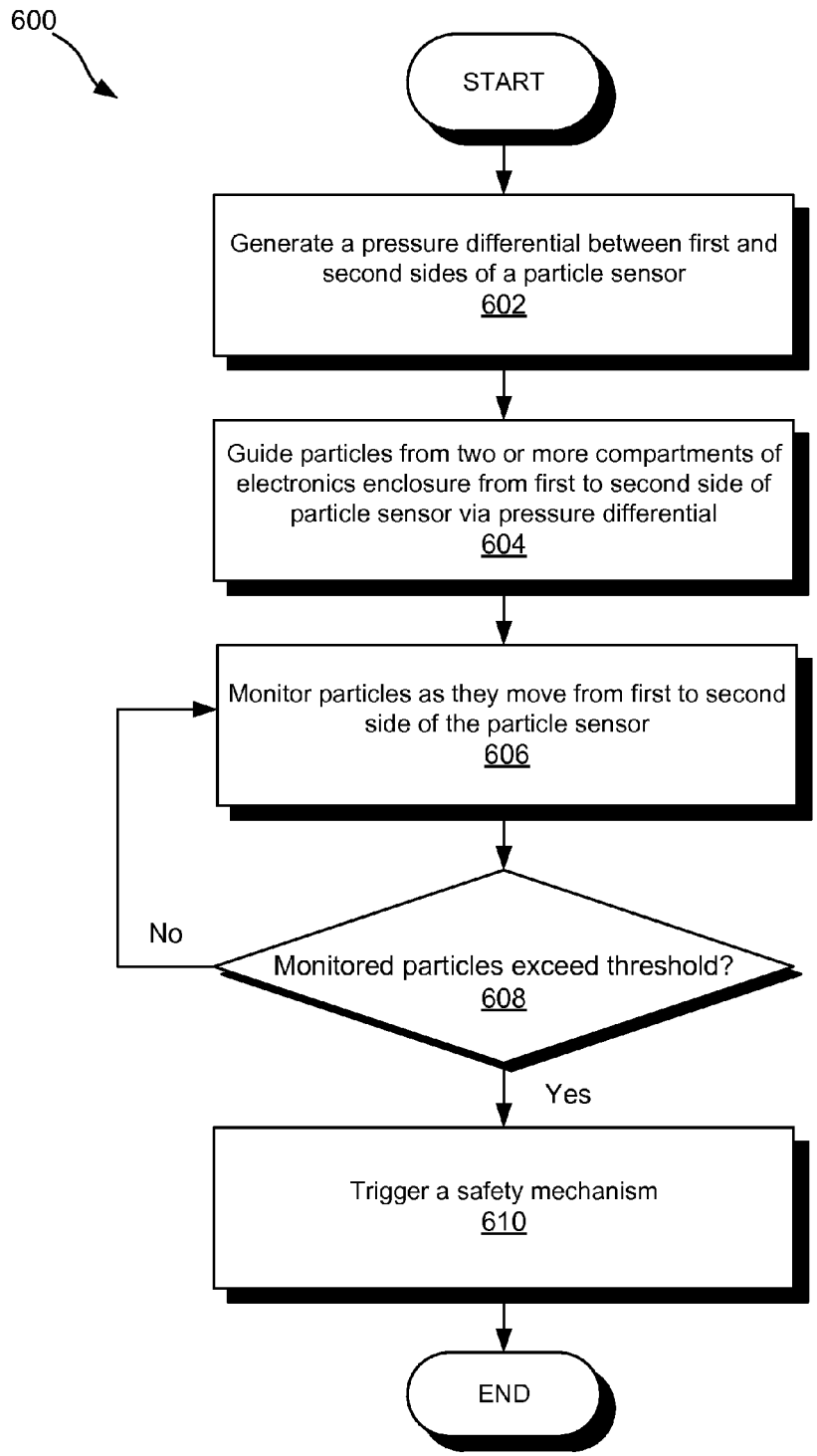
FIG. 6 illustrates a method for detecting smoke within an electronics enclosure.

FIG. 6 illustrates a method for detecting smoke within an electronics enclosure. The method 600 can include generating a pressure differential between a first side and a second side of a particle sensor via a generate pressure differential operation 602. The method 600 can further include guiding particles from two or more compartments of the electronics enclosure from the first side to the second side of the particle sensor via the pressure differential in a guide particles operation 604. The method can additionally include monitoring the particles as they move from the first side to the second side of the particle sensor in a monitor particles operation 606. A decision 608 can then determine if the monitored particles exceed a threshold. If they do, then the method 600 can yet further include triggering a safety mechanism when the particles exceed a threshold in a trigger operation 610. If not, then the method 600 returns to the monitor operation 606 and repeats until the monitored particles exceed the threshold.

Figure 7:
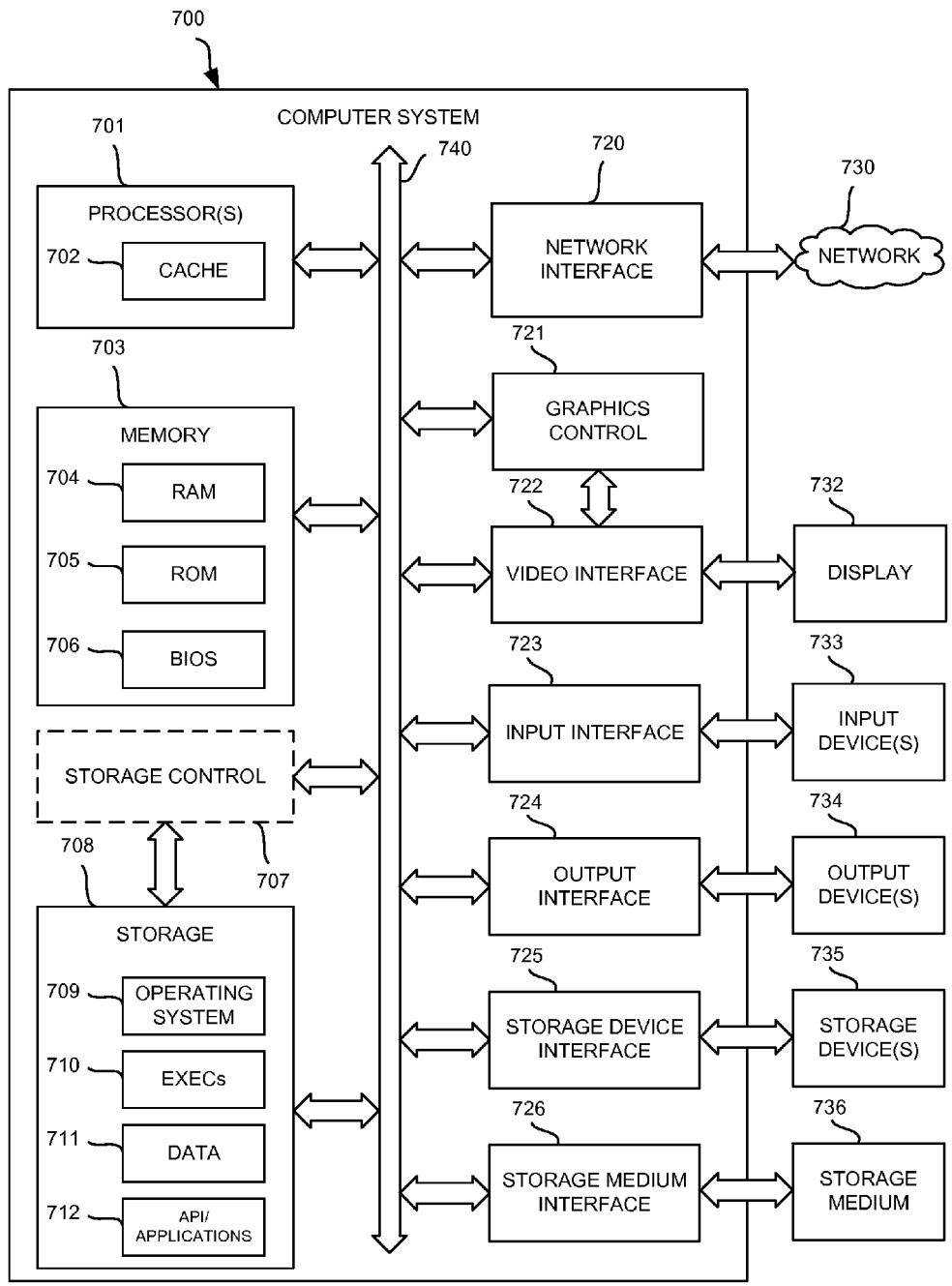
FIG. 7 illustrates a diagrammatic representation of one embodiment of a machine in the exemplary form of a computer system.

The systems and methods described herein can be implemented in a machine such as a computer system in addition to the specific physical devices described herein. FIG. 7 shows a diagrammatic representation of one embodiment of a machine in the exemplary form of a computer system 700 within which a set of instructions can execute for causing a device to perform or execute any one or more of the aspects and/or methodologies of the present disclosure. The components in FIG. 7 are examples only and do not limit the scope of use or functionality of any hardware, software, embedded logic component, or a combination of two or more such components implementing particular embodiments. For instance, FIG. 7 can also be implemented in analog circuitry or a combination of digital and analog circuitry.

Computer system 700 may include a processor 701, a memory 703, and a storage 708 that communicate with each other, and with other components, via a bus 740. The bus 740 may also link a display 732, one or more input devices 733 (which may, for example, include a keypad, a keyboard, a mouse, a stylus, etc.), one or more output devices 734, one or more storage devices 735, and various tangible storage media 736. All of these elements may interface directly or via one or more interfaces or adaptors to the bus 740. For instance, the various tangible storage media 736 can interface with the bus 740 via storage medium interface 726. Computer system 700 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Processor(s) 701 (or central processing unit(s) (CPU(s))) optionally contains a cache memory unit 702 for temporary local storage of instructions, data, or computer addresses. Processor(s) 701 are configured to assist in execution of computer readable instructions. Computer system 700 may provide functionality as a result of the processor(s) 701 executing software embodied in one or more tangible computer-readable storage media, such as memory 703, storage 708, storage devices 735, and/or storage medium 736. The computer-readable media may store software that implements particular embodiments, and processor(s) 701 may execute the software. Memory 703 may read the software from one or more other computer-readable media (such as mass storage device(s) 735, 736) or from one or more other sources through a suitable interface, such as network interface 720. The software may cause processor(s) 701 to carry out one or more processes or one or more steps of one or more processes described or illustrated herein. Carrying out such processes or steps may include defining data structures stored in memory 703 and modifying the data structures as directed by the software.

The memory 703 may include various components (e.g., machine readable media) including, but not limited to, a random access memory component (e.g., RAM 704) (e.g., a static RAM "SRAM", a dynamic RAM "DRAM, etc.), a read-only component (e.g., ROM 705), and any combinations thereof. ROM 705 may act to communicate data and instructions unidirectionally to processor(s) 701, and RAM 704 may act to communicate data and instructions bidirectionally with processor(s) 701. ROM 705 and RAM 704 may include any suitable tangible computer-readable media described below. In one example, a basic input/output system 706 (BIOS), including basic routines that help to transfer information between elements within computer system 700, such as during start-up, may be stored in the memory 703.

Fixed storage 708 is connected bidirectionally to processor(s) 701, optionally through storage control unit 707. Fixed storage 708 provides additional data storage capacity and may also include any suitable tangible computer-readable media described herein. Storage 708 may be used to store operating system 709, EXECs 710 (executables), data 711, API applications 712 (application programs), and the like. Often, although not always, storage 708 is a secondary storage medium (such as a hard disk) that is slower than primary storage (e.g., memory 703). Storage 708 can also include an optical disk drive, a solid-state memory device (e.g., flash-based systems), or a combination of any of the above. Information in storage 708 may, in appropriate cases, be incorporated as virtual memory in memory 703.

In one example, storage device(s) 735 may be removably interfaced with computer system 700 (e.g., via an external port connector (not shown)) via a storage device interface 725. Particularly, storage device(s) 735 and an associated machine-readable medium may provide nonvolatile and/or volatile storage of machine-readable instructions, data structures, program modules, and/or other data for the computer system 700. In one example, software may reside, completely or partially, within a machine-readable medium on storage device(s) 735. In another example, software may reside, completely or partially, within processor(s) 701.

Bus 740 connects a wide variety of subsystems. Herein, reference to a bus may encompass one or more digital signal lines serving a common function, where appropriate. Bus 740 may be any of several types of bus structures including, but not limited to, a memory bus, a memory controller, a peripheral bus, a local bus, and any combinations thereof, using any of a variety of bus architectures. As an example and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 700 may also include an input device 733. In one example, a user of computer system 700 may enter commands and/or other information into computer system 700 via input device(s) 733. Examples of an input device(s) 733 include, but are not limited to, an alpha-numeric input device (e.g., a keyboard), a pointing device (e.g., a mouse or touchpad), a touchpad, a joystick, a gamepad, an audio input device (e.g., a microphone, a voice response system, etc.), an optical scanner, a video or still image capture device (e.g., a camera), and any combinations thereof. Input device(s) 733 may be interfaced to bus 740 via any of a variety of input interfaces 723 (e.g., input interface 723) including, but not limited to, serial, parallel, game port, USB, FIREWIRE, THUNDERBOLT, or any combination of the above.

In particular embodiments, when computer system 700 is connected to network 730, computer system 700 may communicate with other devices, specifically mobile devices and enterprise systems, connected to network 730. Communications to and from computer system 700 may be sent through network interface 720. For example, network interface 720 may receive incoming communications (such as requests or responses from other devices) in the form of one or more packets (such as Internet Protocol (IP) packets) from network 730, and computer system 700 may store the incoming communications in memory 703 for processing. Computer system 700 may similarly store outgoing communications (such as requests or responses to other devices) in the form of one or more packets in memory 703 and communicated to network 730 from network interface 720. Processor(s) 701 may access these communication packets stored in memory 703 for processing.

Examples of the network interface 720 include, but are not limited to, a network interface card, a modem, and any combination thereof. Examples of a network 730 or network segment 730 include, but are not limited to, a wide area network (WAN) (e.g., the Internet, an enterprise network), a local area network (LAN) (e.g., a network associated with an office, a building, a campus or other relatively small geographic space), a telephone network, a direct connection between two computing devices, and any combinations thereof. A network, such as network 730, may employ a wired and/or a wireless mode of communication. In general, any network topology may be used.

Information and data can be displayed through a display 732. Examples of a display 732 include, but are not limited to, a liquid crystal display (LCD), an organic liquid crystal display (OLED), a cathode ray tube (CRT), a plasma display, and any combinations thereof. The display 732 can interface to the processor(s) 701, memory 703, and fixed storage 708, as well as other devices, such as input device(s) 733, via the bus 740. The display 732 is linked to the bus 740 via a video interface 722, and transport of data between the display 732 and the bus 740 can be controlled via the graphics control 721.

In addition to a display 732, computer system 700 may include one or more other peripheral output devices 734 including, but not limited to, an audio speaker, a printer, and any combinations thereof. Such peripheral output devices may be connected to the bus 740 via an output interface 724. Examples of an output interface 724 include, but are not limited to, a serial port, a parallel connection, a USB port, a FIREWIRE port, a THUNDERBOLT port, and any combinations thereof.

In addition or as an alternative, computer system 700 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. An electronic system comprising:
    a multi-compartment electronics enclosure having compartments, each of the compartments comprising electronic components;
    a particle sensor that monitors particles passing through or contacting the particle sensor and generates a signal describing monitored particles, the particle sensor experiencing a pressure differential between a first and a second side of the particle sensor;
    fluid pathways, each of the fluid pathways connecting one of the compartments to the particle sensor, the pressure differential causing air and particles to be drawn out of each of the compartments through the fluid pathways and through or into contact with the particle sensor; and
    a detection and warning module that receives the signal from the particle sensor and determines if a level of smoke in any of the compartments exceeds a threshold, and if so, generates a warning indicator.

2. The system of claim 1, wherein a system fan of the electronic system generates the pressure differential.

3. The system of claim 1, wherein an airflow controller generates the pressure differential.

4. The system of claim 3, further comprising a system fan for cooling the electronic components.

5. The system of claim 1, wherein the particle sensor is coupled to the multi-compartment electronics enclosure.

6. The system of claim 5, wherein the particle sensor is arranged external to the multi-compartment electronics enclosure.

7. The system of claim 1, wherein the warning indicator causes electronics in the electronic system to be shut down.

8. The system of claim 1, wherein the airflow controller is a fan.

9. The system of claim 1, wherein the compartments are RF isolated from each other.

10. The system of claim 9, wherein there is no airflow between the compartments.

11. The system of claim 1, wherein the detection and warning module distinguishes between smoke and dust particles.

12. A method of detecting an undesired level of a target particle within a multi-compartment electronics enclosure, the method comprising:
    providing a particle sensor;
    generating a pressure differential between a first side and a second side of the particle sensor;
    pulling air and particles from compartments of the multi-compartment electronics enclosure to the first side of the particle sensor and moving the air and particles from there to the second side;
    monitoring the particles in the air as they move from the first to the second side of the particle sensor;
    determining that a level of the target particle in any of the compartments exceeds a threshold; and
    triggering a safety mechanism of the multi-compartment electronics enclosure in response to the determining.

13. The method of claim 12, wherein the certain type of particle is a smoke particle.

14. The method of claim 12, wherein the monitoring is performed via a photo-electric particle sensor.

15. A non-transitory, tangible computer readable storage medium, encoded with processor readable instructions to perform a method for monitoring target particles within an electronics enclosure, the method comprising:
    generating a pressure differential between a first side and a second side of a particle sensor;
    guiding particles from two or more compartments of the electronics enclosure from the first side to the second side of the particle sensor via the pressure differential;
    monitoring the particles as they move from the first side to the second side of the particle sensor; and
    triggering a safety mechanism when the particles exceed a threshold.

16. The non-transitory, tangible computer readable storage medium of claim 15, wherein the monitoring monitors for particle flux.

17. The non-transitory, tangible computer readable storage medium of claim 15, wherein the safety mechanism is a shut-down of electronics of the electronics enclosure.

* * * * *